US011116936B2

(12) United States Patent
Harding et al.

(10) Patent No.: US 11,116,936 B2
(45) Date of Patent: Sep. 14, 2021

(54) LOW-PROFILE EXTENSION FOR A CATHETER ASSEMBLY

(71) Applicant: Becton, Dickinson and Company, Franklin Lakes, NJ (US)

(72) Inventors: Weston F Harding, Lehi, UT (US); Shaun Staley, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 246 days.

(21) Appl. No.: 15/481,690

(22) Filed: Apr. 7, 2017

(65) Prior Publication Data
US 2018/0289920 A1 Oct. 11, 2018

(51) Int. Cl.
*A61M 25/00* (2006.01)
*A61M 25/06* (2006.01)
*A61M 39/10* (2006.01)

(52) U.S. Cl.
CPC ........ *A61M 25/00* (2013.01); *A61M 25/0067* (2013.01); *A61M 25/0082* (2013.01); *A61M 25/0084* (2013.01); *A61M 25/0097* (2013.01); *A61M 25/06* (2013.01); *A61M 39/1011* (2013.01); *A61M 25/0606* (2013.01); *A61M 2025/0004* (2013.01); *A61M 2025/0089* (2013.01); *A61M 2025/0091* (2013.01); *A61M 2039/1027* (2013.01); *A61M 2039/1077* (2013.01)

(58) Field of Classification Search
CPC .......... A61M 39/1011; A61M 25/0067; A61M 25/0606; A61M 25/002; A61M 25/0097; A61M 2039/1027; A61M 2039/1072; A61M 2039/1077
See application file for complete search history.

(56) References Cited

U.S. PATENT DOCUMENTS

| 5,522,803 | A | * | 6/1996 | Teissen-Simony | ... A61M 5/158 604/177 |
| 6,056,718 | A | * | 5/2000 | Funderburk | ...... A61M 25/0097 604/161 |
| 6,302,866 | B1 | * | 10/2001 | Marggi | ............. A61M 25/0097 604/174 |
| 6,749,589 | B1 | * | 6/2004 | Douglas | ............ A61M 25/0097 604/162 |
| 7,220,241 | B2 | * | 5/2007 | Csincsura | ............. A61M 5/158 604/180 |

(Continued)

FOREIGN PATENT DOCUMENTS

| EP | 0891204 | 12/2003 |
| EP | 2837403 | 2/2015 |

(Continued)

*Primary Examiner* — William R Carpenter
(74) *Attorney, Agent, or Firm* — Kirton McConkie; Craig Metcalf; Kevin Stinger (57) ABSTRACT

An extension for a catheter assembly may include a distal end and a proximal end. The distal end may include one or more cantilever arms and an insertion feature spaced apart from the cantilever arms. The insertion feature may be configured to insert into a lumen of a catheter adapter to provide a fluid connection between the catheter adapter and the extension. The one or more cantilever arms may be configured to engage in a snap-fit with the catheter adapter. The proximal end of the extension may include a female luer fitting.

8 Claims, 10 Drawing Sheets

(56) References Cited

U.S. PATENT DOCUMENTS

| | | | | |
|---|---|---|---|---|
| 7,303,543 | B1* | 12/2007 | Maule | A61M 5/158 604/533 |
| 7,318,818 | B2* | 1/2008 | Yashiro | A61M 25/0097 604/164.07 |
| 8,062,250 | B2* | 11/2011 | Mogensen | A61M 5/158 604/93.01 |
| 8,465,461 | B2* | 6/2013 | Wu | A61M 5/165 604/190 |
| 9,173,996 | B2* | 11/2015 | Gray | A61M 5/1456 |
| 2002/0120231 | A1* | 8/2002 | Douglas | A61M 39/1011 604/82 |
| 2002/0161332 | A1* | 10/2002 | Ramey | A61M 5/158 604/164.07 |
| 2002/0173769 | A1* | 11/2002 | Gray | A61M 5/1456 604/506 |
| 2003/0208165 | A1* | 11/2003 | Christensen | A61M 39/045 604/256 |
| 2006/0047251 | A1* | 3/2006 | Bickford Smith | A61M 39/10 604/240 |
| 2007/0049870 | A1* | 3/2007 | Gray | A61M 5/1456 604/158 |
| 2008/0140020 | A1 | 6/2008 | Shirley | |
| 2008/0214999 | A1* | 9/2008 | Kletchka | A61B 17/22032 604/96.01 |
| 2012/0323181 | A1* | 12/2012 | Shaw | A61B 17/3415 604/164.12 |
| 2014/0074031 | A1* | 3/2014 | Bornhoft | A61M 39/10 604/164.01 |
| 2014/0180250 | A1* | 6/2014 | Belson | A61M 25/01 604/510 |
| 2016/0015888 | A1* | 1/2016 | Tieck | A61M 5/1413 137/551 |
| 2016/0051757 | A1* | 2/2016 | Gray | A61M 5/1456 604/151 |
| 2017/0239443 | A1* | 8/2017 | Abitabilo | A61M 25/0108 |

FOREIGN PATENT DOCUMENTS

| | | |
|---|---|---|
| WO | 91/16938 | 11/1991 |
| WO | 99/44655 | 9/1999 |

* cited by examiner

LOW-PROFILE EXTENSION FOR A CATHETER ASSEMBLY

BACKGROUND OF THE INVENTION

Catheters are commonly used for a variety of infusion therapies. For example, catheters may be used for infusing fluids, such as normal saline solution, various medicaments, and total parenteral nutrition into a patient. Catheters may also be used for withdrawing blood from the patient. Each catheter is typically coupled to a catheter adapter to enable coupling of the catheter to tubing connected to a fluid source. In further detail, the tubing connected to the fluid source may terminate in a male luer fitting, which may be coupled to a female luer fitting of the catheter adapter, and fluid from the fluid source may be infused into the vasculature of the patient via the catheter.

Often the male luer fitting and/or the female luer fitting are bulky and/or may have protruding, sharp edges that may irritate or damage skin of the patient, particularly when the patient is an elderly or neonate patient. In some instances, the sharp edges may result in pain or even infection. The bulkiness of the male luer fitting and/or the female luer fitting may also raise the catheter from the patient, which may increase a chance of accidental dislodgement of the catheter from the vasculature of the patient. Accordingly, there is a need for catheter systems and methods that stabilize the catheter within the vasculature of the patient and reduce a risk of skin damage.

BRIEF SUMMARY OF THE INVENTION

The present disclosure may relate generally to devices, systems, and associated methods to stabilize a catheter inserted into vasculature of a patient and/or prevent irritation of skin of the patient by a catheter adapter coupled to the catheter or by a luer fitting. In some embodiments, a low-profile extension may be coupled to the catheter adapter, which may allow the catheter adapter to sit closer to the skin. If the catheter adapter is disposed close to the skin, an insertion depth of the catheter extending from the catheter adapter may increase, reducing a risk of dislodgement of the catheter and providing stability to the catheter. The extension may also allow remote manipulation of a luer connection, which may prevent disruption of an insertion site of the catheter.

In some embodiments, the catheter adapter may include a proximal end, a distal end, and a lumen extending therebetween. In some embodiments, the proximal end of the catheter adapter may include one or more slots and/or a proximal lumen opening. In some embodiments, the distal end of the catheter adapter may include the catheter, which may be configured to be inserted into the vasculature of the patient.

In some embodiments, the extension may include a distal end, a proximal end, and a lumen extending therebetween. In some embodiments, the distal end of the extension may include one or more cantilever arms and/or an insertion feature spaced apart from the cantilever arms. In some embodiments, the insertion feature may be configured to insert into the lumen of the catheter adapter to provide a fluid connection between the catheter adapter and the extension. In some embodiments, each of the cantilever arms may be configured to engage in a snap-fit with the catheter adapter.

In further detail, in some embodiments, the cantilever arms may be configured to insert into the slots to engage in a snap-fit with the catheter adapter. In some embodiments, distal ends of each of the cantilever arms may include a hook. In some embodiments, each of the cantilever arms may deflect as the hook of the corresponding cantilever arm is inserted into a corresponding slot of the catheter adapter. In some embodiments, as the hook reaches a groove proximate the slot, the cantilever arm may return to an original shape of the cantilever arm prior to insertion into the slot.

In some embodiments, the insertion feature may be spaced apart from the cantilever arms by separator elements that may extend outwardly with respect to a longitudinal axis of the extension. In some embodiments, the cantilever arms may include a first cantilever arm and a second cantilever arm. In some embodiments, the first cantilever arm may oppose the second cantilever arm.

In some embodiments, the proximal end of the extension may be configured to be coupled to a male luer fitting or another connector. For example, the proximal end of the extension may include a female luer fitting.

In some embodiments, the extension may include an elongated tubular element, which may be disposed between the distal end and the proximal end. In some embodiments, the extension may include a grip portion, which may be disposed between the distal and proximal ends of the extension. In some embodiments, the grip portion may include one or more wings and/or one or more protrusions. In some embodiments, the grip portion may be disposed proximal to the tubular element.

In some embodiments, the catheter adapter may include a stabilization platform. In some embodiments, the slots may be disposed within the stabilization platform. In some embodiments, a width of each of the separator elements may be approximately equal to a width of the stabilization platform, which may prevent formation of any protruding edges when the extension is secured to the catheter adapter. Protruding edges could contact the skin of the patient and cause irritation.

BRIEF DESCRIPTION OF THE SEVERAL VIEWS OF THE FIGURES

In order that the manner in which the above-recited and other features and advantages of the invention will be readily understood, a more particular description of the devices, systems, and associated methods to secure and stabilize a catheter briefly described above will be rendered by reference to specific embodiments thereof, which are illustrated in FIGS. 1-8. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

It will be readily understood that the components of the present invention, as generally described and illustrated in the Figures in the present disclosure, could be arranged and designed in a wide variety of different configurations. Thus, the following more detailed description of the embodiments, represented in FIGS. 1-8, is not intended to limit the scope of the invention, as claimed, but is merely representative of some embodiments of the invention.

Figure 1:
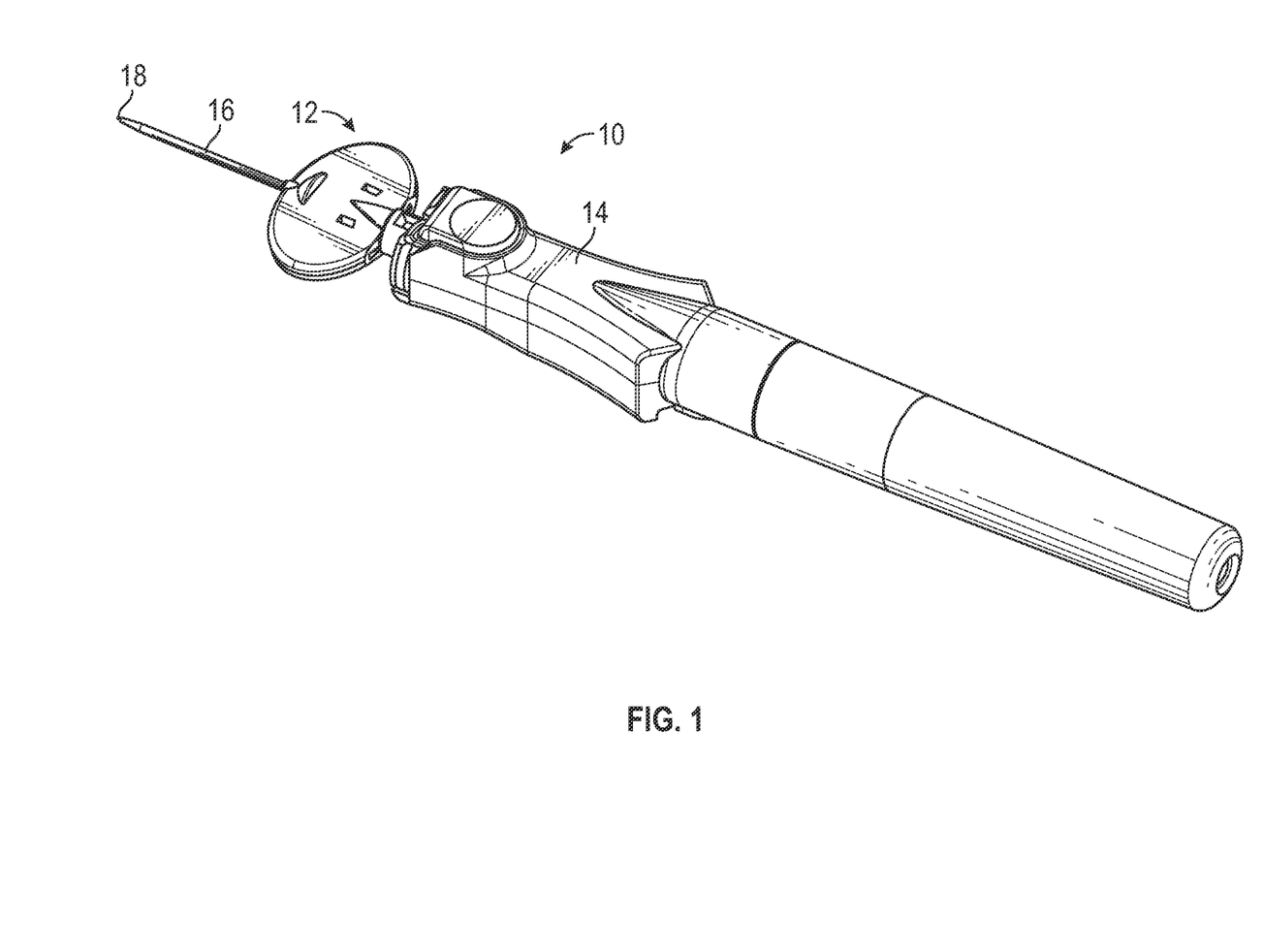
FIG. 1 is an upper perspective view of an example needle shield coupled to an example catheter assembly ready for insertion into vasculature of a patient, according to some embodiments.

FIG. 1 illustrates a catheter assembly 10 in accordance with one or more embodiments. In some embodiments, the catheter assembly 10 may include a catheter adapter 12 coupled to a needle safety feature, which may include a needle shield 14. In some embodiments, a catheter 16 may extend distally from the catheter adapter 12, and a proximal end of the catheter 16 may be secured within the catheter adapter 12. In some embodiments, the needle shield 14 may include a needle hub (not illustrated), which may secure a proximal end of an introducer needle 18. In some embodiments, when the needle 18 is ready to be inserted into vasculature of the patient, the needle 18 may extend through the catheter 16 and beyond a tip of the catheter 16, as illustrated in FIG. 1.

In some embodiments, once the needle 18 has been used to insert the catheter 16 into the vasculature of a patient, the needle hub may be retracted into the needle shield 14 such that the needle 18 is fully contained within the needle shield 14. In some embodiments, when the needle 18 is retracted into the needle shield 14, a blood control septum disposed within a lumen of the catheter adapter may close to prevent blood leakage. In some embodiments, the needle shield 14 may be uncoupled from the catheter adapter 12 in response to the catheter 16 being inserted into the vasculature of the patient and/or the needle 18 being retracted into the needle shield 14. Generally, a male luer fitting may then be coupled to the catheter adapter 12, and fluid may be infused into the vasculature of the patient via the catheter 16. As an alternative, in some embodiments, an extension may be coupled with the proximal end of the catheter adapter, and the male luer fitting may be coupled to a proximal end of the extension, as will be described in further detail. In these embodiments, the fluid may be infused into the vasculature of the patient via a fluid pathway that includes the extension.

The catheter assembly 10 may include any suitable type of catheter assembly. In some embodiments, the catheter assembly 10 may include an intravenous (IV) catheter assembly. As an example, the catheter assembly 10 may include one or more features of the BD INSYTE™ AUTOGUARD™ Shield IV Catheter, and the needle shield 14 may be spring loaded. As another example, the catheter assembly 10 may include one or more features of the BD NEXIVA™ DIFFUSICS™ Closed IV Catheter System. Suitable materials for the catheter adapter 12 and/or the extension 20 may include, but are not limited to, thermoplastic polymeric resins such as polycarbonate, polystyrene, polypropylene, polyethylene terephthalate glycol PETG), and the like.

Figure 2:
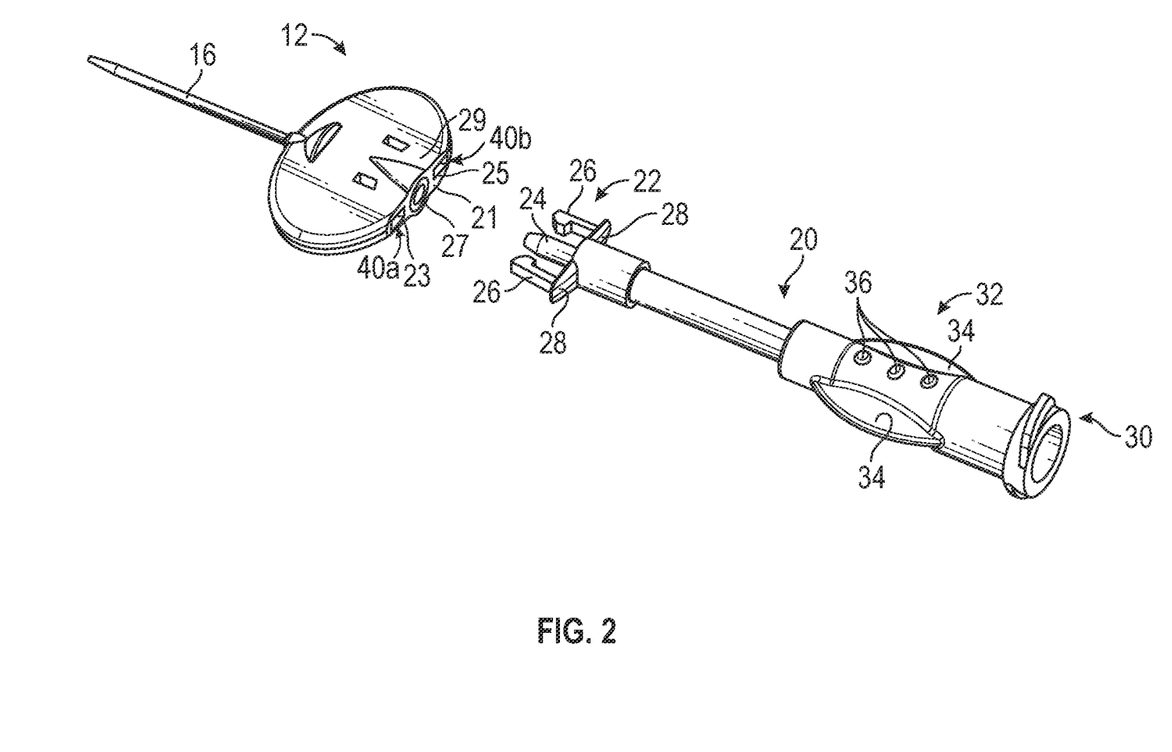
FIG. 2 is an upper perspective view of the catheter assembly of FIG. 1 and an example extension ready to be coupled to the catheter assembly, according to some embodiments.

Referring now to FIG. 2, in some embodiments, the extension 20 may include an elongated body. In some embodiments, a distal end of the extension 20 may include a connector element 22. In some embodiments, the connector element 22 may include an insertion feature 24 and one or more cantilever arms 26 spaced apart from the insertion feature 24. In some embodiments, the cantilever arms 26 may be disposed generally parallel to the insertion feature 24. In some embodiments, the cantilever arms 26 may extend in a distal direction. In some embodiments, the cantilever arms 26 may be spaced apart from the insertion feature 24 by outwardly-extending separator elements 28. In some embodiments, the insertion feature 24 may be aligned with a longitudinal axis of the extension 20. As illustrated in FIG. 2, the proximal end of the catheter adapter 12 may include a proximal face 21 having a first opening 23 for a first slot 40a, a second opening 25 for a second slot 40b, and a proximal lumen opening 27. A body 29 of the catheter adapter 12 at the proximal face 21 may have a distance between the first opening 23 and the proximal lumen opening 27 that is uninterrupted and another distance between the second opening 25 and the proximal lumen opening 27 that is uninterrupted, as illustrated in FIG. 2.

The connector element may include any number of cantilever arms 26. In some embodiments, a first cantilever arm 26 and a second cantilever arm 26 may be aligned on opposite sides of the extension 20, as illustrated in FIG. 2. In some embodiments, the connector element 22 may include an annular cantilever arm 26, which may surround the insertion feature 24.

In some embodiments, the proximal end of the extension 20 may be configured to connect to another device. In some embodiments, the proximal end of the extension may include a female luer fitting 30. In some embodiments, the proximal end of the extension 20 may include one or more threads for connection to the male luer fitting or another connector.

In some embodiments, the extension 20 may include a grip portion 32, which may facilitate insertion of the extension 20 into the catheter adapter 12 by a user. In some embodiments, the grip portion 32 may include one or more wings 34 and/or protrusions 36.

Figure 3A:
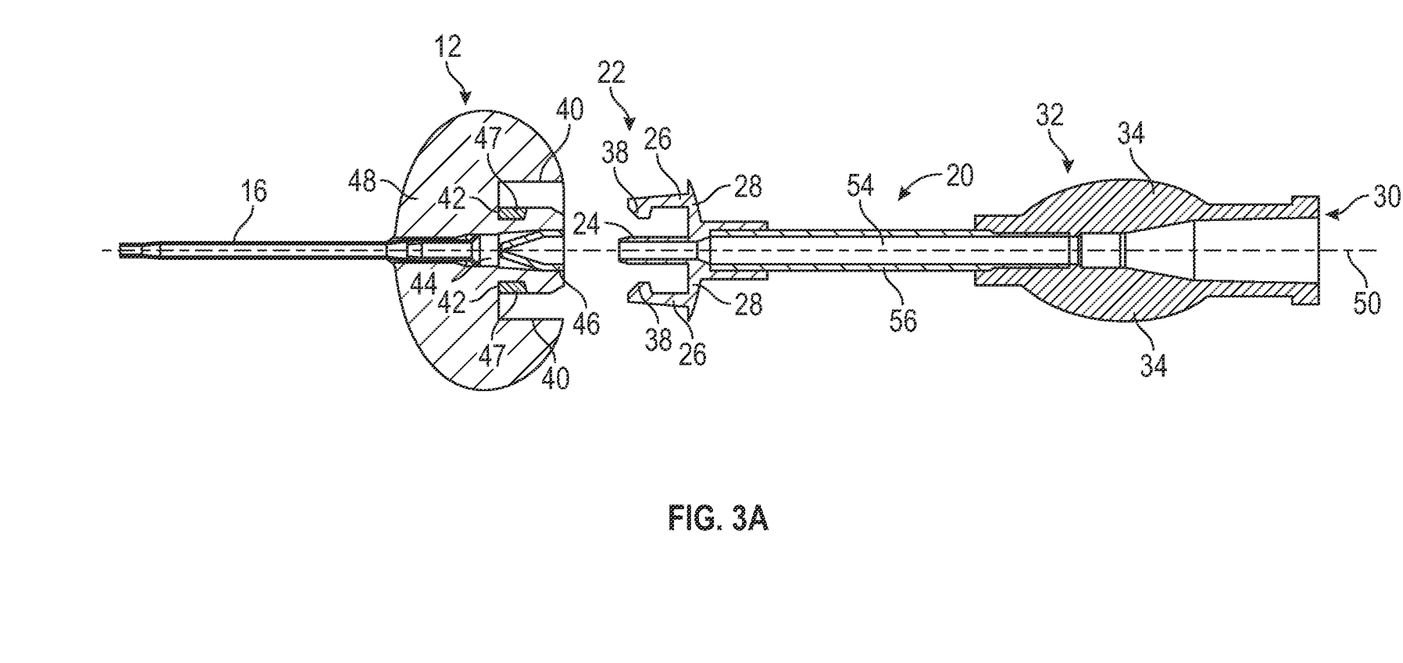
FIG. 3A is a widthwise cross-sectional view of the catheter assembly of FIG. 1 and the extension of FIG. 2, according to some embodiments.
Figure 3B:
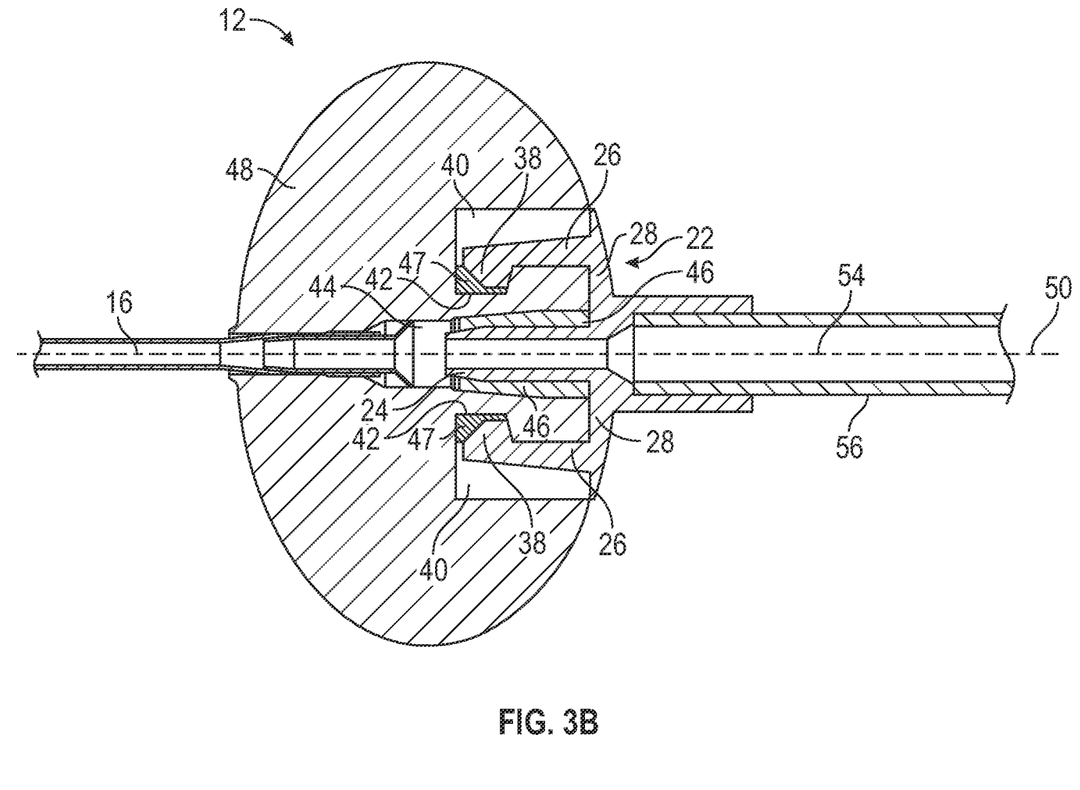
FIG. 3B is a widthwise, enlarged cross-sectional view of the extension of FIG. 2 secured to the catheter assembly of FIG. 1, according to some embodiments.

Referring now to FIGS. 3A-3B, in some embodiments, the cantilever arms 26 may engage in a snap-fit with the catheter adapter 12. In further detail, in some embodiments, each of the cantilever arms 26 may include a distal end that includes a hook 38. In some embodiments, each of the cantilever arms 26 may deflect as the hook 38 of the corresponding cantilever arm 26 is inserted into a corresponding slot 40 of the catheter adapter 12. In some embodiments, as the hook 38 reaches a groove 42 proximate the slot 40, the cantilever arm 26 may return to an original shape of the cantilever arm 26 prior to insertion into the slot 40. In some embodiments, the insertion feature 24 may be sized and configured to insert into the lumen 44 of the catheter adapter 12 and open the blood control septum 46 when the cantilever arms 26 engage in the snap-fit with the catheter adapter 12. Thus, in some embodiments, the insertion feature 24 may include an actuator.

In some embodiments, once the connector element 22 is secured in the catheter adapter 12 via the snap-fit, a connection between the extension 20 and the catheter adapter 12 may be permanent, decreasing a risk of the user to blood exposure. In further detail, it may be difficult for the user to remove the extension 20 from the catheter adapter 12 without a tool once the connector element 22 is secured in the catheter adapter 12 in the snap-fit. In some embodiments, the grooves 42 may include an adhesive 47, which may increase a strength of the connection between the extension 20 and the catheter adapter 12.

In some embodiments, the catheter adapter 12 may include a stabilization platform 48. In some embodiments, the stabilization platform 48 may include one or more wings, which may extend outwardly from a body of the catheter adapter 12. In some embodiments, the slots 40 may be disposed within the stabilization platform 48. In some embodiments, a first slot 40 corresponding to a first cantilever arm 26 may be disposed on a first side of the stabilization platform 48, and a second slot 40 corresponding to a second cantilever arm 26 may be disposed on a second side of the stabilization platform 48. In some embodiments, the slots 40 may be generally parallel to a longitudinal axis 50 of the catheter adapter 12 and the extension 20. In some embodiments, the slots 40 may be spaced apart from the lumen 44 of the catheter adapter 12.

In some embodiments, the extension 20 may include a lumen 54 extending therethrough. In further detail, the lumen 54 of the extension 20 may extend through the insertion feature 24 of the distal end of the extension 20 to a proximal end of the extension 20. The extension 20 may be integrally formed or include separate components. In some embodiments, the connector element 22 may be coupled with a tubular element 56 of the extension 20. In other embodiments, the tubular element 56 and the connector element 22 may be integrally formed. In some embodiments, the tubular element 56 may have a uniform inner diameter, which may be greater than an inner diameter of the insertion feature 24.

Figure 4:
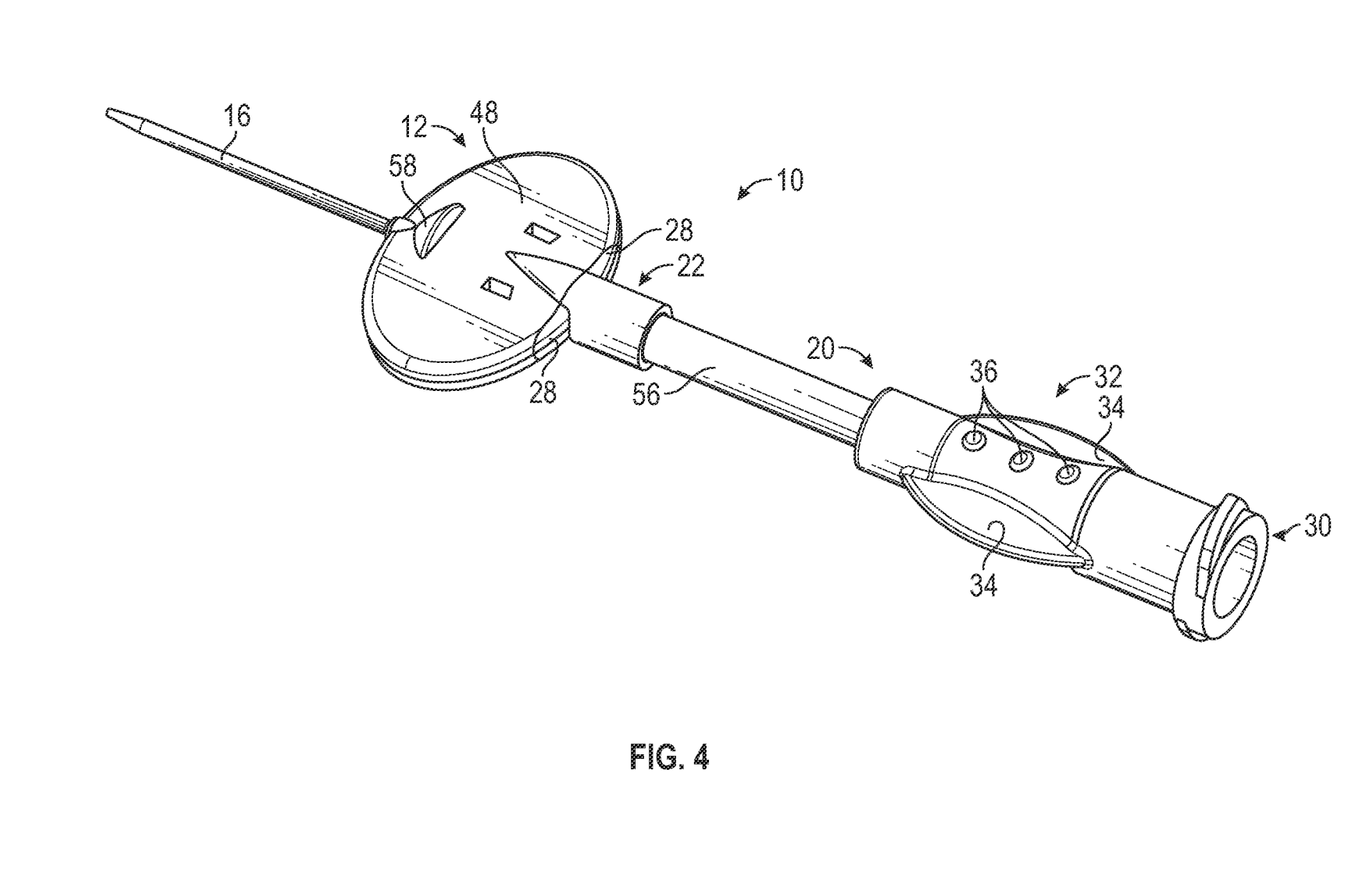
FIG. 4 is an upper perspective view of the extension of FIG. 2 secured to the catheter assembly of FIG. 1, according to some embodiments.

Referring now to FIG. 4, in some embodiments, a shape of the stabilization platform 48 may be generally planar or flat, which may allow the stabilization platform 48 to have a low-profile. In some embodiments, a distal end of the stabilization platform 48 may include a gradual taper. In some embodiments, the stabilization platform 48 may include a push tab 58 disposed on an upper surface of the stabilization platform 48. In some embodiments, the push tab 58 may be integrally molded from a same material as the stabilization platform 48. In some embodiments, the upper surface of the stabilization platform 48 may be smooth except for the push tab 58. In some embodiments, a bottom surface of the stabilization platform 48, or a surface of the stabilization platform 48 closest to skin of the patient, may be smooth. In some embodiments, the catheter adapter 12 and/or the extension 20 may be free of protruding edges that may irritate the skin of the patient.

In some embodiments, the separator elements 28 may complete a geometric shape of the catheter adapter 12 when the connector element 22 is secured to the catheter adapter 12. In these and other embodiments, a width of the separator elements 28 may be approximately equal to a width of the catheter adapter 12 such that the separator elements 28 do not protrude above or below the catheter adapter 12 and irritate the skin of the patient, as illustrated in FIG. 4.

In some embodiments, the stabilization platform 48 may support one or more digits of the user as the user inserts the catheter 16 at the insertion site, hoods the needle 18, or moves the catheter assembly 12 from an insertion configuration to a fluid delivery configuration. In some embodiments, the user may pinch or grip the stabilization platform 24, which may extend outwardly from the longitudinal axis 50.

The securement platform 48 may optionally be "soft," i.e., formed of a relatively compliant material that conforms easily to the skin of the patient. In some embodiments, the securement platform 48 may be formed of a soft plastic, an elastomer such as silicone rubber, and/or the like.

Figure 5A:
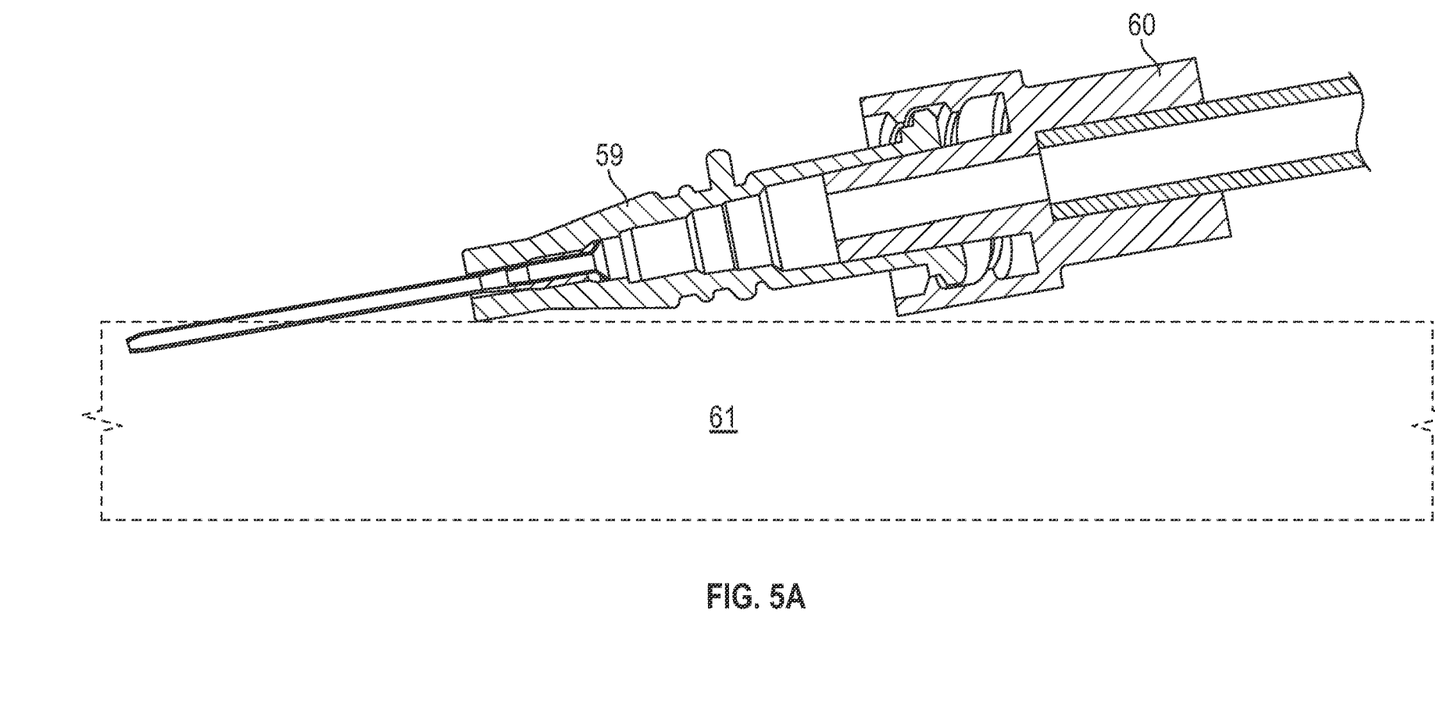
FIG. 5A is a longitudinal cross-sectional view of a conventional catheter assembly inserted into skin of the patient and coupled to an example male luer fitting, according to some embodiments.

As illustrated in FIG. 5A, a conventional catheter adapter 59 may be directly connected to the male luer fitting 60, which may increase a gap or distance between the catheter adapter 59 and the skin 61 of the patient due to threading between the catheter adapter 59 and the male luer fitting 60. The male luer fitting 60 directly connected to the conventional catheter adapter 59 may also increase an angle of the catheter adapter 59 with respect to the skin 61.

Figure 5B:
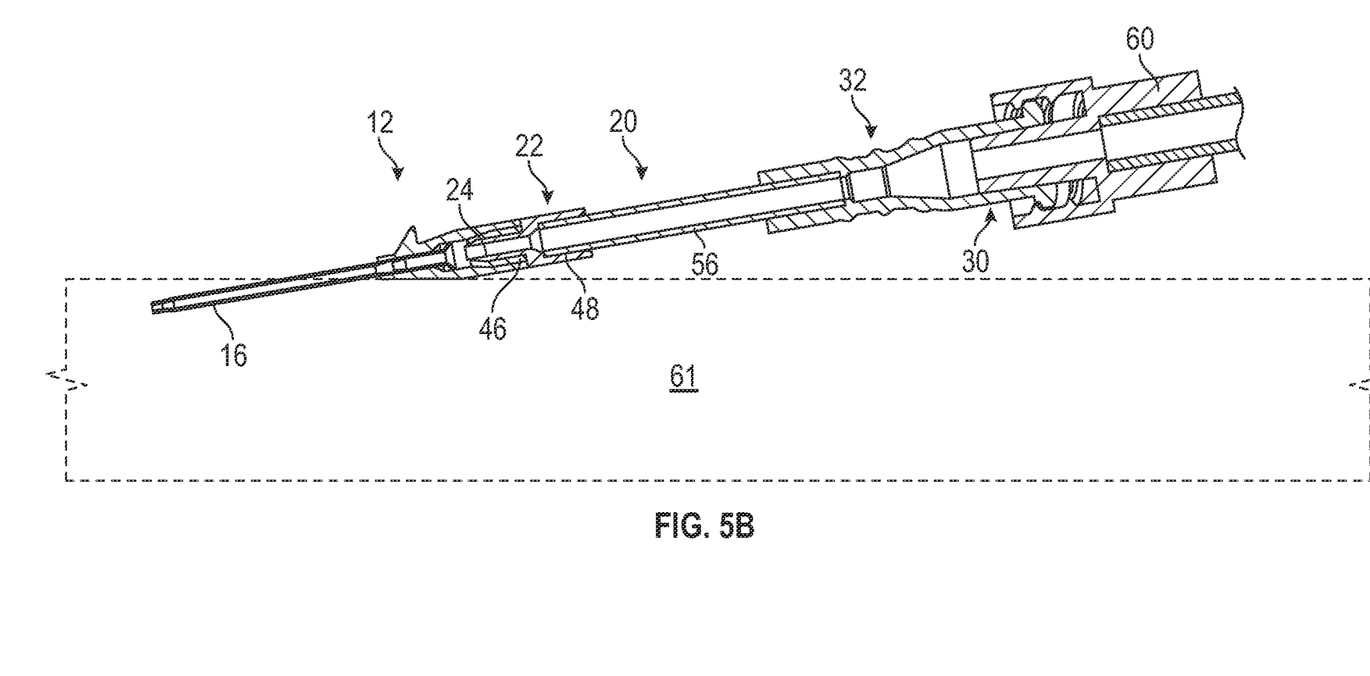
FIG. 5B is a longitudinal cross-sectional view of the extension of FIG. 2 secured to the catheter assembly of FIG. 1 and the male luer fitting of FIG. 5A, according to some embodiments.

As illustrated in FIG. 5B, in some embodiments, the extension 20 may be secured to the catheter adapter 12 without any turning or twisting, which may allow the catheter adapter 12 and the extension 20 to maintain a low-profile. Thus, the catheter adapter 12 may sit closer to the skin 61 than the conventional catheter adapter 59, maximizing a catheter insertion depth and stability of the catheter 16. Also, a side of the catheter adapter 12 may be allowed to contact the skin 61, further increasing the stability of the catheter 16. In these and other embodiments, an outer diameter of the catheter adapter 12 may be decreased or tapered at a tip or nose of the catheter adapter 12 compared to the conventional catheter adapter 59, which may allow the catheter adapter 12 to maintain a low-profile.

In some embodiments, the male luer fitting 60 may include one or more protruding sharp edges, which may more easily contact the skin 61 in absence of the extension 20, as illustrated in FIG. 5A. Advantageously, in some embodiments, the extension 20 may allow for remote manipulation of the male luer fitting 60 and luer connection, which may reduce a risk of disturbing an insertion site of the catheter 16.

Figure 6:
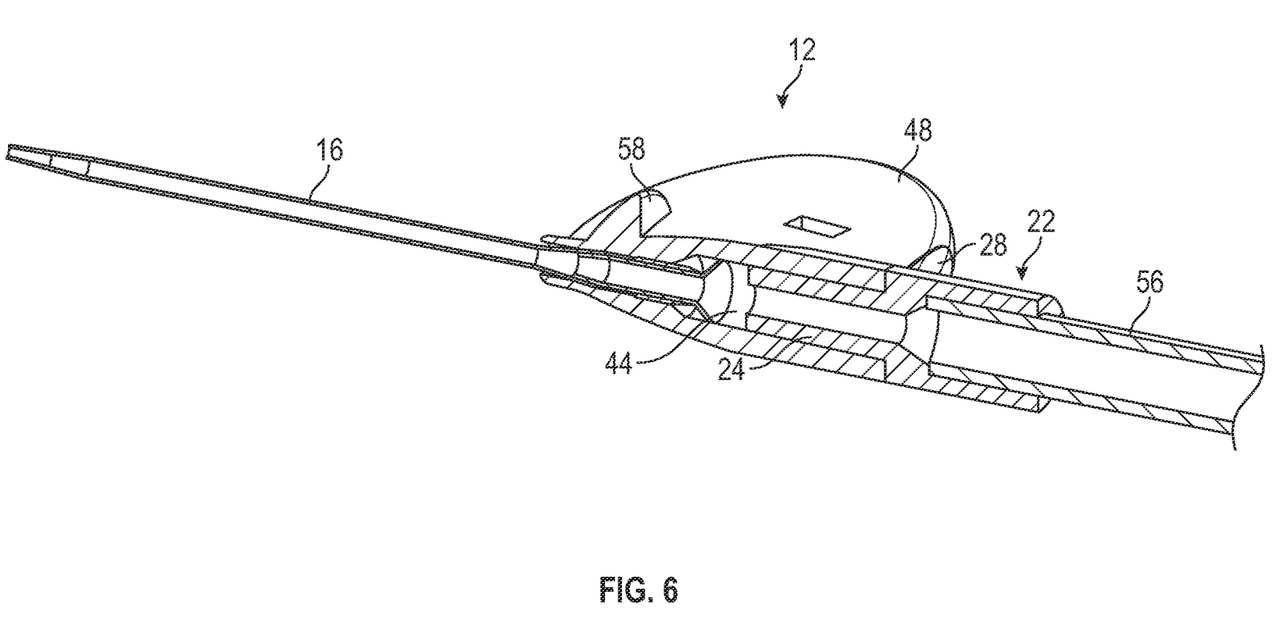
FIG. 6 is an upper perspective, cutaway view of the catheter assembly of FIG. 1 secured to the extension of FIG. 2, according to some embodiments.

Referring now to FIG. 6, in some embodiments, the catheter adapter 12 may not include the blood control septum 46, such as, for example, in neonatal applications. In some embodiments, a conical seal may be relied upon to provide blood control. In further detail, in some embodiments, a male conical surface of the insertion feature 24 may wedge into or be engaged in an interference fit with a female conical surface of the catheter adapter 12. In these and other embodiments, an outer diameter of the insertion feature 24 and an inner diameter of the catheter adapter 12 may be approximately the same.

Figure 7:
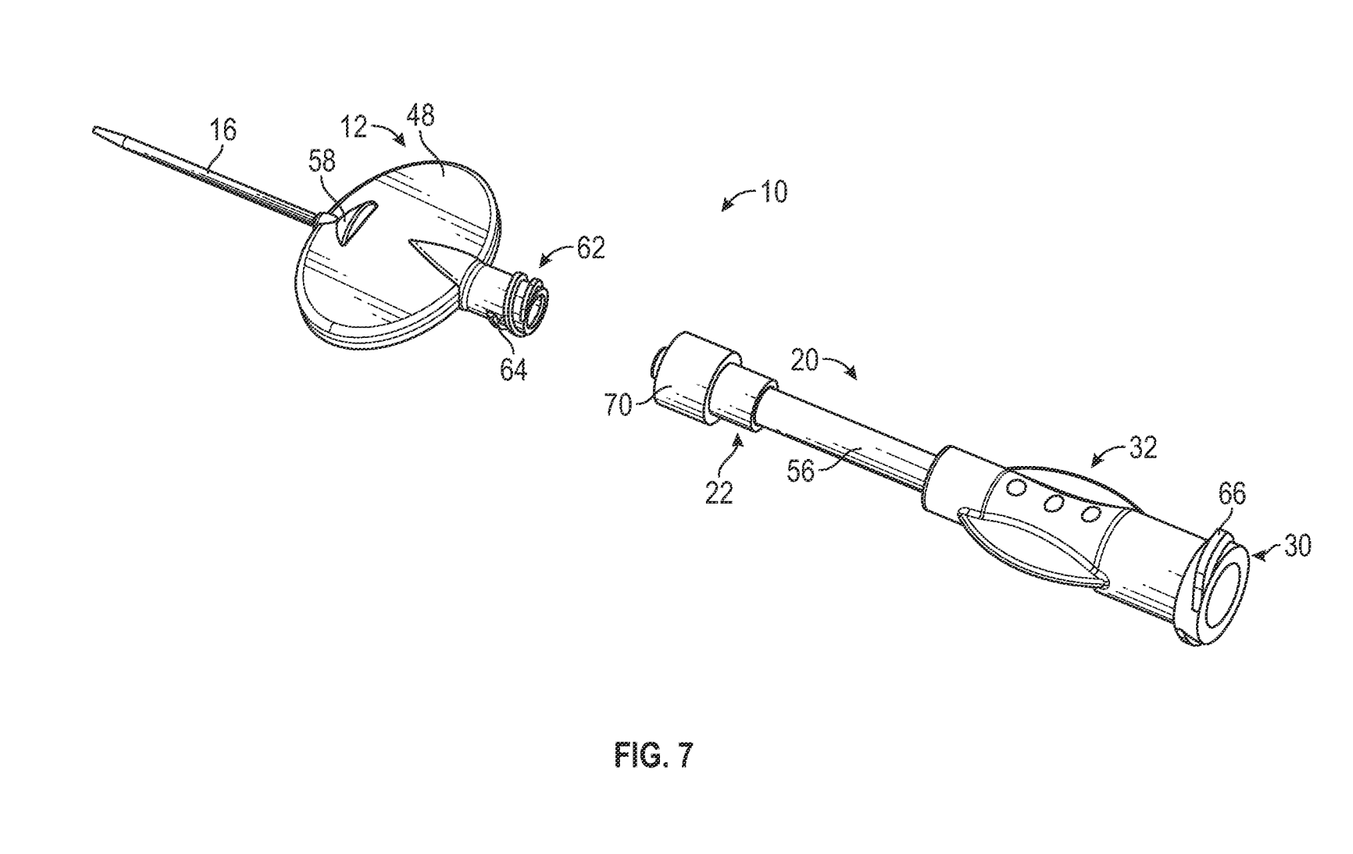
FIG. 7 is an upper perspective view of the catheter assembly of FIG. 1 and the example extension of FIG. 2 ready to be coupled to the catheter assembly, according to some embodiments.
Figure 8:
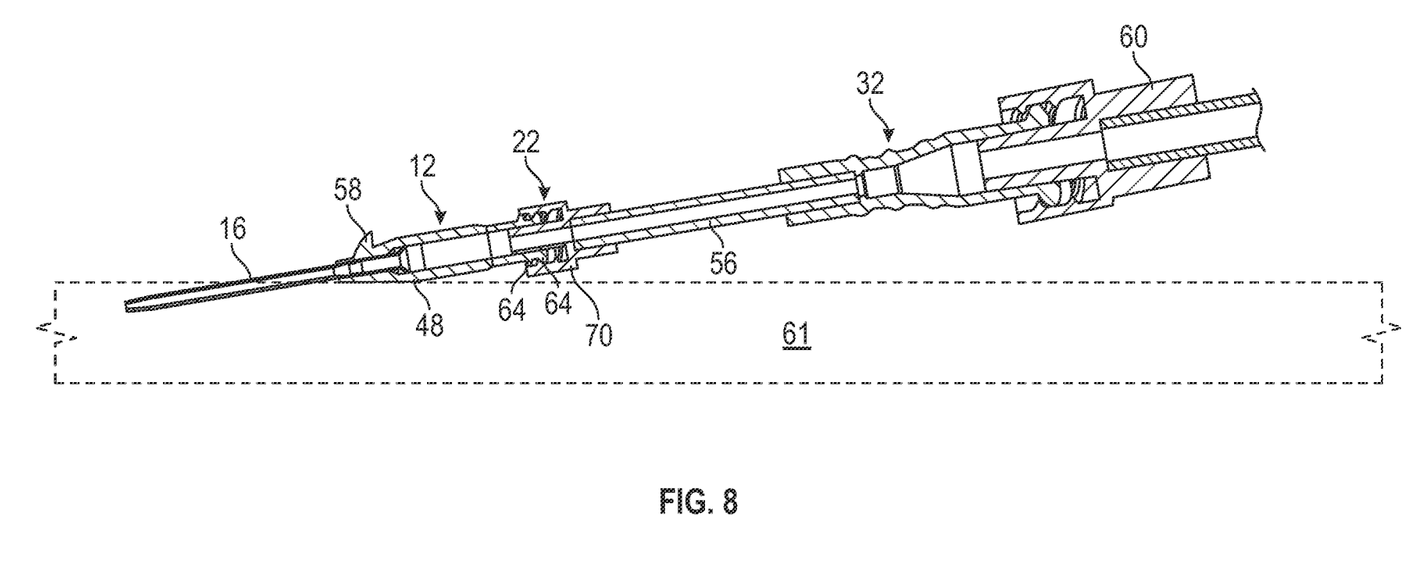
FIG. 8 is a longitudinal cross-sectional view of the extension of FIG. 2 secured to the catheter assembly of FIG. 1 and the male luer fitting of FIG. 5A, according to some embodiments.

Referring now to FIGS. 7-8, in some embodiments, the proximal end of the catheter adapter 12 may include a connector, such as, for example, a female luer-type fitting 62. In some embodiments, the proximal end of the extension 20 may include another female luer-type fitting. In some embodiments, the female luer-type fitting 62 and the other female luer-type fitting may be a same or similar size. In some embodiments, the other female luer-type fitting may include the female luer fitting 30. In some embodiments, the female luer-type fitting 62 of the catheter adapter 12 may have a reduced size compared to the female luer fitting 30 of the proximal end of the extension 20. In further detail, in some embodiments, a proximal end and/or threads 64 of the female luer-type fitting 62 may have a reduced diameter compared to a proximal end and/or threads 66 of the female luer fitting 30. Thus, in some embodiments, a corresponding male luer-type fitting 70 of the distal end of the extension 20 may be reduced in size compared to the male luer fitting 60, allowing the catheter adapter 12 and the extension 20 to maintain a low-profile. The low-profile of the catheter adapter 12 and/or the extension 20 may allow the catheter adapter 12 to sit close to the skin 61, which may increase an catheter insertion depth and stability of the catheter 16. In these and other embodiments, a side of the catheter adapter 12 may contact the skin 61, increasing the stability of the catheter 16.

In some embodiments, the male luer fitting 60 and/or the female luer fitting 30 may correspond to International Organization for Standardization ("ISO") 80369-7. In some embodiments, a cross-sectional diameter at a distal end of a tip of the male luer fitting 60 may be between about 0.1563 inches (3.970 mm) and about 0.1603 inches (4.072 mm). In some embodiments, an inner cross-sectional diameter at an open proximal end of the female luer fitting 30 may be between about 0.1653 inches (4.198 mm) and about 0.1692 inches (4.298 mm).

In some embodiments, the male luer-type fitting 70 and/or the female luer-type fitting 62 may be smaller than ISO 80369-7. In some embodiments, a cross-sectional diameter at a distal end of a tip of the male luer-type fitting 70 may be less than about 0.1545 inches (3.925 mm) for rigid material and less than about 0.1545 inches (3.925 mm) for semi-rigid material. In some embodiments, an inner cross-sectional diameter at an open proximal end of the female luer-type fitting 62 may be less than about 0.168 inches (4.270 mm).

In some embodiments, the male luer-type fitting 70, the female luer-type fitting 62, and/or the tubular element 56 may be sized to reduce a priming volume for sensitive applications such as infusion for neonates. In these and other embodiments, the male luer-type fitting 70 and the female luer-type fitting 62 may be sized smaller than International Organization for Standardization ("ISO") 80369-7, and a size of the tubular element 56 may correspond to the male luer-type fitting 70. For example, a portion of the lumen 54 of the extension 62 that extends through the male luer-type fitting 70 and the tubular element 56 may have a generally uniform diameter.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter system, comprising:
    a catheter adapter, comprising a proximal end, a distal end, and a lumen extending therebetween, wherein the catheter adapter further comprises a first slot, a first groove proximate the first slot, a second slot, and a second groove proximate a second slot, wherein the proximal end comprises a proximal face having a first opening for the first slot, a second opening for the second slot, and a proximal lumen opening disposed in between the first slot and the second slot, wherein the first slot and the second slot are configured to receive an extension via a snap-fit, wherein a body of the catheter adapter at the proximal face has a distance between the first opening and the proximal lumen opening that is uninterrupted, wherein the body of the catheter adapter at the proximal face has another distance between the second opening and the proximal lumen opening that is uninterrupted, wherein the first groove and the second groove comprise an adhesive, wherein the adhesive is configured to adhere a first cantilever arm and a second cantilever arm of the extension to the catheter adapter;
    a septum disposed within the lumen and configured to receive an insertion feature of the extension, wherein the insertion feature actuates the septum to open a fluid path between the extension and the lumen;
    a catheter extending distally from the distal end of the catheter adapter, wherein the catheter is configured to be inserted into vasculature of a patient, wherein the catheter comprises a longitudinal axis, wherein the catheter adapter is configured to be selectively coupled with a distal end of a needle shield;
    an introducer needle extending through the proximal lumen opening and the catheter; and
    a needle shield coupled to the catheter adapter, wherein the introducer needle is configured to be retracted proximally into the needle shield.

2. The catheter system of claim 1, wherein the catheter adapter comprises a stabilization platform.

3. The catheter system of claim 2, wherein the first slot and the second slot are disposed within the stabilization platform.

4. The catheter system of claim 3, wherein the proximal lumen opening is configured to receive the insertion feature of the extension, wherein the insertion feature is spaced apart from the first cantilever arm and the second cantilever arm by a plurality of separator elements that extend outwardly with respect to a longitudinal axis of the extension.

5. The catheter system of claim 1, wherein the adhesive is limited to the first groove and the second groove.

6. The catheter system of claim 1, further comprising the extension, wherein the extension includes a proximal end and a distal end, and wherein the distal end of the extension includes the first cantilever arm, the second cantilever arm, and the insertion feature.

7. The catheter system of claim 6, wherein the extension further comprises an elongated tubular element disposed between the distal end and the proximal end of the extension.

8. The catheter system of claim 6, wherein the extension further comprises a grip portion disposed between the distal end and the proximal end of the extension, wherein the grip portion comprises one or more wings or one or more protrusions.

* * * * *